(12) United States Patent
Liou

(10) Patent No.: US 11,110,209 B2
(45) Date of Patent: Sep. 7, 2021

(54) INTRALUMINAL THERAPY SYSTEM FOR GASTROINTESTINAL INFECTIONS

(71) Applicant: MACKAY MEDICAL FOUNDATION THE PRESBYTERIAN CHURCH IN TAIWAN MACKAY MEMORIAL HOSPITAL, Taipei (TW)

(72) Inventor: Tai-Cherng Liou, Taipei (TW)

(73) Assignee: MACKAY MEDICAL FOUNDATION THE PRESBYTERIAN CHURCH IN TAIWAN MACKAY MEMORIAL HOSPITAL, Taipei (TW)

( * ) Notice: Subject to any disclaimer, the term of this patent is extended or adjusted under 35 U.S.C. 154(b) by 362 days.

(21) Appl. No.: 15/874,331

(22) Filed: Jan. 18, 2018

(65) Prior Publication Data

US 2018/0221542 A1 Aug. 9, 2018

Related U.S. Application Data

(60) Provisional application No. 62/447,726, filed on Jan. 18, 2017.

(51) Int. Cl.
*A61N 1/30* (2006.01)
*A61L 29/16* (2006.01)
(Continued)

(52) U.S. Cl.
CPC .............. *A61L 29/16* (2013.01); *A61B 1/015* (2013.01); *A61B 1/018* (2013.01); *A61B 1/2736* (2013.01);
(Continued)

(58) Field of Classification Search
CPC ....... A61B 1/015; A61B 1/018; A61B 1/2736; A61B 1/005; A61B 1/0051;
(Continued)

(56) References Cited

U.S. PATENT DOCUMENTS 5,665,064 A 9/1997 Bodicky et al.
6,238,335 B1 * 5/2001 Silverman ........ A61B 17/12022
600/29
(Continued)

FOREIGN PATENT DOCUMENTS

CN 2745525 Y 12/2005
CN 101448448 A 6/2009
(Continued)

OTHER PUBLICATIONS

Office action dated Apr. 2, 2020 by the China Intellectual Property Patent Office for the counterpart application No. 201810048802.8.
(Continued)

*Primary Examiner* — Rebecca E Eisenberg
(74) *Attorney, Agent, or Firm* — WPAT, P.C.; Anthony King

(57) ABSTRACT

A novel intraluminal therapy system for providing a quick and effective way to treat gastrointestinal infections. The invention includes a brand new system of treating *Helicobacter pylori* infections and an agent dispenser for an endoscope apparatus, comprising a pump, a catheter connected to the pump and a nozzle connected to the catheter. The devices are used along with a complex of antibiotic and/or antimicrobial agents to eradicate *Helicobacter pylori* while performing an endoscopic procedure.

18 Claims, 3 Drawing Sheets

(51) Int. Cl.
  *A61P 31/04* (2006.01)
  *A61K 31/4439* (2006.01)
  *A61K 31/43* (2006.01)
  *A61K 31/4164* (2006.01)
  *A61B 1/273* (2006.01)
  *A61B 1/015* (2006.01)
  *A61B 1/018* (2006.01)
  *A61M 25/06* (2006.01)
  *A61K 31/7048* (2006.01)
  *A61M 25/00* (2006.01)

(52) U.S. Cl.
  CPC .......... *A61K 31/4164* (2013.01); *A61K 31/43* (2013.01); *A61K 31/4439* (2013.01); *A61K 31/7048* (2013.01); *A61M 25/007* (2013.01); *A61M 25/0662* (2013.01); *A61P 31/04* (2018.01); *A61L 2300/404* (2013.01); *A61L 2300/406* (2013.01)

(58) Field of Classification Search
  CPC ........... A61B 1/00087; A61B 1/00091; A61M 25/007; A61M 25/0662
  See application file for complete search history.

(56) References Cited

U.S. PATENT DOCUMENTS

| | | | |
|---|---|---|---|
| 6,248,058 B1 | 6/2001 | Silverman et al. | |
| 6,383,181 B1 | 5/2002 | Johnston et al. | |
| 2003/0093031 A1* | 5/2003 | Long | A61B 1/00087 604/95.01 |
| 2003/0216613 A1* | 11/2003 | Suzuki | A61B 1/32 600/104 |
| 2004/0077965 A1* | 4/2004 | Hubbard | A61B 5/083 600/532 |
| 2006/0149193 A1* | 7/2006 | Hall | A61B 17/32037 604/275 |
| 2008/0214619 A1* | 9/2008 | Wolfe | G06Q 10/00 514/338 |
| 2018/0059119 A1* | 3/2018 | Tak Ts | A61B 10/0283 |
| 2018/0078119 A1* | 3/2018 | Krimsky | A61M 16/0459 |
| 2020/0178773 A1* | 6/2020 | Miller | A61B 1/00096 |

FOREIGN PATENT DOCUMENTS

| | | |
|---|---|---|
| CN | 203303491 U | 11/2013 |
| CN | 204146999 U | 2/2015 |
| CN | 204158877 U | 2/2015 |
| CN | 104983493 A | 10/2015 |
| CN | 205339829 U | 6/2016 |
| CN | 205386134 U | 7/2016 |
| JP | H0951955 A | 2/1997 |
| JP | 2009254874 A | 11/2009 |
| JP | 2010213939 A | 9/2010 |

OTHER PUBLICATIONS

English abstract translation of CN 101448448A, CN 205339829U, CN 2745525Y, CN 203303491, CN 204158877U and CN 204146999U.
Office action dated Jun. 10, 2019 Taiwan Intellectual Property Patent Office for the counterpart Taiwan Patent Application No. 10710890.
English abstract translation of CN205386134U.
English abstract translation of CN104983493A.
Office Action and Cited Reference List dated Feb. 5, 2019 issued by Japan Patent Office for counterpart application No. 2018-006679.
Machine Translation of Japan Patent Application JPH0951955A.
Machine Translation of Japan Patent Application JP2010213939A.
Machine Translation of Japan Patent Application JP2009254874A.
English Translated Cited Reference List.

* cited by examiner

INTRALUMINAL THERAPY SYSTEM FOR GASTROINTESTINAL INFECTIONS

FIELD OF THE INVENTION

The invention relates to a novel intraluminal therapy system of treating gastrointestinal infections. Particularly, the invention provides the concomitant use of endoscopic devices along with a complex of antibiotic and/or antimicrobial agents for the effective treatment of gastrointestinal infections.

BACKGROUND OF THE INVENTION

Gastrointestinal infections may be caused by various microorganisms. For example, *Helicobacter pylori* (*H. pylori*) is a spiral-shaped, gram-negative, microaerophilic bacterium, which resides within the mucous layer of the human gastric mucosa and colonizes the mucosal surface of the stomach and the duodenal bulb. Due to its extremely low pH, the stomach is a hostile environment to most other microorganisms. The ability of *H. pylori* to flourish in the stomach has been attributed to its protective mechanisms, such as the production of urease to neutralize gastric acid to create an environment in which the pathogen can thrive. The organism possesses two to seven unipolar sheathed flagella which enhance its mobility through viscous solutions. The bacterium's urease, motility, and ability to adhere to the gastric epithelium are key factors that allow it to survive and proliferate in the gastric milieu.

Epidemiological studies have shown that *H. pylori* causes the most common chronic bacterial infection in humans. Conservative estimates suggest that about 50% of the world population is infected with *H. pylori*. *H. pylori* is now known to cause gastritis, gastric ulcers, duodenal ulcers, gastric adenocarcinoma and mucosa-associated lymphoid tissue (MALT) lymphoma. Endoscopic examination is indicated, especially in symptomatic patients or asymptomatic individuals with a higher incidence of stomach cancer. The eradication of *H. pylori* can lead to the improvement of dyspeptic symptoms, the reduction in the recurrence of peptic ulcer disease, and the prevention of gastric cancer. However, it is estimated that 15-20% of patients fail first-line standard eradication therapy and need second-line rescue therapy. About 15-30% of patients fail second-line therapy and ultimately receive third-line therapy. In recent years, the eradication rate for *H. pylori* infection has been decreasing worldwide due to the increasing prevalence of antibiotic resistant strains.

No single drug can cure *H. pylori* infection. The current treatment for *H. pylori* infection mainly consists of the combination of a proton-pump inhibitor (PPI) and one to three oral antibiotics for 7 to 14 days. Studies have shown that using known oral anti-infective agents alone is insufficient to eradicate *H. pylori* due to the special gastric milieu and the increasing rates of antibiotic resistance in *H. pylori*. Although many oral antibiotics can suppress *H. pylori* growth in vivo, the antibiotic concentration in the mucous layer of the gastric mucosa is inadequate in practice and the penetration of antibodies into the gastric mucus layer is poor in effect. To achieve higher eradication rates, most treatment regimens involve taking several oral medications for 14 days. However, patient compliance, side effects and drug resistance further limit their applicability and efficacy. In view of the foregoing limitations, there is a pressing need to develop an adequate new therapy system and alternative strategies to eradicate *H. pylori* for treating gastrointestinal infections before the prevalence of antibiotic resistance gets out of control.

BRIEF SUMMARY OF THE INVENTION

The present invention develops a novel intraluminal therapy system comprising the administration of an antibiotic and/or antimicrobial complex and a method for the concomitant treatment of bacterial infection while performing an endoscopic procedure. By using the novel therapy system, conventional multiple-dose antibiotics regimens are no longer necessary. Instead, the administration of one-dose therapeutic agents of the invention can eradicate bacterial infection in a short time.

The present invention provides an agent dispenser for an endoscope apparatus, comprising a pump for pumping an agent, a catheter connected to the pump and a nozzle connected to the catheter. The catheter extends into an operation section of the endoscope apparatus via an opening in the operation section and passes through an insertion tube, then extends outward from an opening at the end of a bending section of the endoscope apparatus.

The present invention also provides a system for dispensing one or more agents to a subject's gastrointestinal tract. The system comprises an endoscope apparatus and an agent dispenser. The endoscope apparatus includes a light guide device, an operation section connected to the light guide device, an insertion tube connected to the operation section, and a bending section connected to the insertion tube. The operation section has an opening to connect with the insertion tube and the bending section. The agent dispenser comprises a pump for pumping an agent, a catheter connected to the pump and a nozzle connected to the catheter. The catheter extends into the operation section and passes through the insertion tube, then extends outward from an opening at the end of the bending section.

The present invention further provides an antibiotic and/or antimicrobial complex comprising an antibiotic and/or antimicrobial agent cross-linked to or mixed with carriers wherein the complex provides a specific viscosity conferring high affinity to the gastric mucosal surface.

The present invention also provides a method for treating a gastrointestinal infection in a subject, comprising the following steps: (i) providing a system of the invention; (ii) administering an antibiotic and/or antimicrobial agent or an antibiotic and/or antimicrobial complex to a gastrointestinal tract using the system of the invention.

In order to further understand the present invention, the following embodiments are provided along with illustrations to facilitate the appreciation of the present invention; however, the appended drawings are merely provided for reference and illustration without any intention to be used for limiting the scope of the present invention.

DESCRIPTION OF THE INVENTION

The invention provides a novel intraluminal therapy system, which utilizes medical devices, such as an endoscope, dispensing delivery applicators, proton pump inhibitors, localization and irrigation spraying devices to go along with a complex of antibiotic and/or antimicrobial agents for the concomitant treatment of gastrointestinal infections. By using the therapeutic system or methods of the invention, conventional multiple-dose antibiotics regimens are no longer necessary. The administration of one-dose therapeutic agents can be completed to eradicate *H. pylori* while performing an endoscopic procedure.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the present invention.

Unless otherwise specified, "a" or "an" means one or more.

As used herein, the term "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the term "subject" refers to a vertebrate, preferably a mammal, more preferably a human. Mammals include, but are not limited to, humans, farm animals, sport animals, and pets.

As used herein, the term "effective amount" refers to an amount sufficient to effect beneficial or desired results. An effective amount can be administered in one or more administrations. For the purposes of this invention, an effective amount is an amount that is sufficient to ameliorate, stabilize, reverse, slow or delay the progression of the disease state or eradicate the disease.

As used herein, the terms "treatment," "treating." "treat" and the like generally refer to obtaining a desired pharmacologic and/or physiological effect. The effect may be therapeutic in terms of a partial or complete stabilization or cure for a disease and/or adverse effect attributable to the disease.

Figure 1:
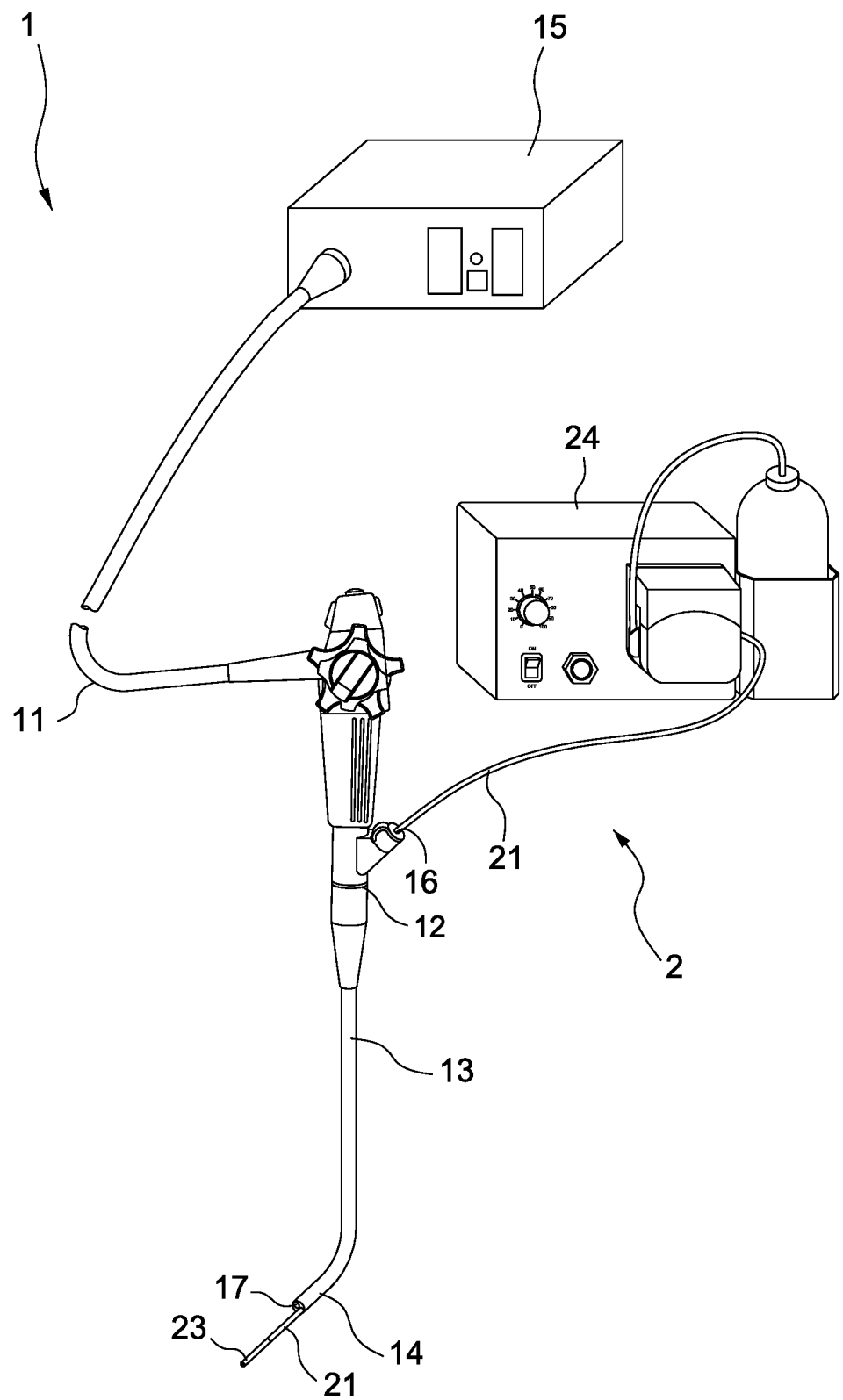
FIG. 1 is a perspective schematic view of the system for dispensing one or more agents to a subject's gastrointestinal tract in accordance with an embodiment of the present invention.

FIG. 1 is a perspective schematic view of a system for dispensing one or more agent to a subject's gastrointestinal tract in accordance with an embodiment of the instant disclosure. As illustrated in FIG. 1, such system comprises an endoscope apparatus 1 and an agent dispenser 2. The endoscope apparatus 1 is used to captures an endoscopic image of a subject and connected to a work station 15. Such work station 15 comprises a light source device that supplies observation light to the endoscope apparatus 1, a processor device that performs image processing on the endoscopic image captured by the endoscope apparatus 1, a display device that displays the endoscopic image that has undergone the image processing and has been output from the processor device, and an input device that receives an input operation. The endoscope apparatus 1 comprises a light guide device 11, an operation section 12, an insertion tube 13 and a bending section 14. One end of the light guide device 11 connects to the work station 15 and the other end of the light guide device 11 connects to the operation section 12.

The operation section 12 further connects to the insertion tube 13 so that the light guide device 11 connects to the insertion tube 13 through the operation section 12. Further, the endoscope apparatus comprises a working channel formed in the interior space of the operation section 12, the insertion tube 13 and the bending section 14. The working channel has an opening 16 formed at the operation section 12 and another opening 17 formed at the end of the bending section 14. The endoscope apparatus 1 is known in the art and any medical device can also be used in the invention to deliver the medicament(s). The agent dispenser 2 comprises a pump 24, a catheter 21 and a nozzle 23. The pump 24 is used for pumping one or more irrigating agent(s), antibiotic and/or antimicrobial agent(s) to a subject's gastrointestinal tract. In one embodiment, the booster pump 24 can provide a desired pressure that is adjustable depending on a need in treatment and/or a patient's condition. In one embodiment, the pump provides a pressure ranging from 0.13 MPa to 70 MPa, more preferably from 0.17 MPa to 50 Mpa, and most suitably from 0.86 MPa to 17.2 MPa.

One end of the catheter 21 connects to the pump 24. The catheter 21 extends into the working channel via the opening 16 formed at the operation section 12 and passes through the working channel, then extends outward from the working channel via the opening 17 formed at the end of the bending section 14. The catheter 21 is used for delivering the agent(s) pumped from the pump 24. In one embodiment, the total length of the catheter ranges from 50 cm to 350 cm, more preferably from 100 cm to 250 cm, and most suitably from 150 cm to 230 cm. The outer diameter of the catheter ranges from 0.5 mm to 5 mm, more preferably from 1.2 mm to 3.7 mm, and most suitably from 1.6 mm to 2.8 mm.

The nozzle 23 connects to the other end of the catheter 21 that extends outward from the opening 17 at the end of the bending section 14. The nozzle 23 is used to irrigate the mucosal surface inside the stomach and to dispense the agent(s) delivered from the catheter 21 to the stomach surface.

While using such a system, the physician-operator can inspect the patient's stomach by the endoscope apparatus 1 and dispense the agents into the stomach by the agent dispenser 2 at the same time. The physician-operator can utilize the operation section 12 of the endoscope apparatus 1 to control the insertion tube 13 and the bending section 14 to inspect the patient's stomach. Once the physician-operator finds an area on the stomach surface which should be treated, he/she can actuate the pump 24 to pump the agent(s) into the catheter 21 and deliver the agent(s) to the nozzle 23. Since the nozzle 23 is substantially projected from the end of the bending section 14, which is inserted into the patient's stomach, the agents sprayed from the nozzle 23 can be directly and accurately dispensed on the area needed to be treated.

Figure 2A:
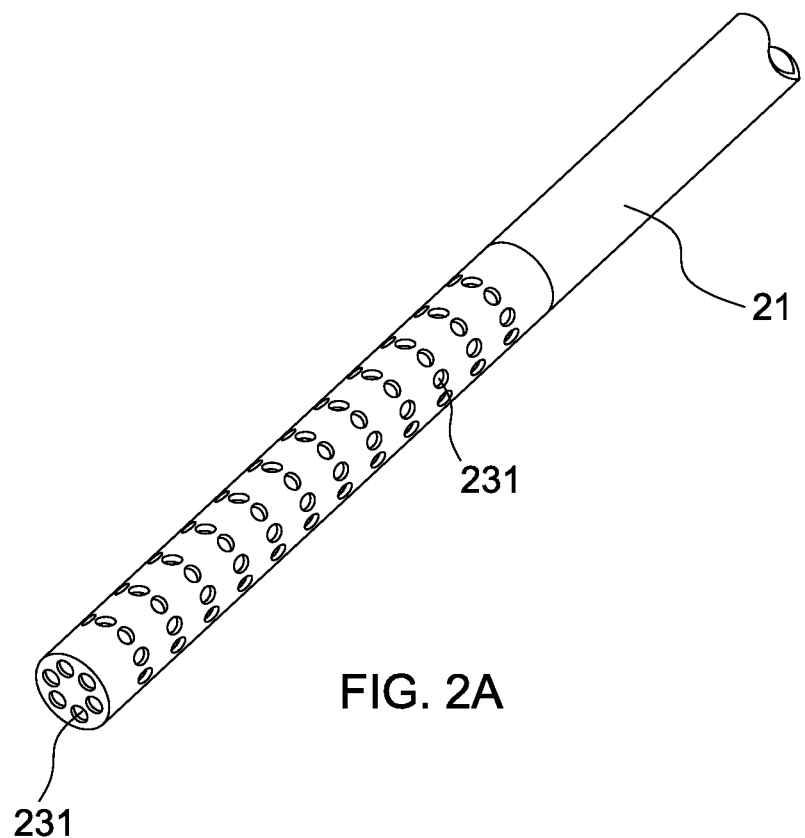
FIG. 2A is an enlarged view of the nozzle in accordance with an embodiment of the present invention.
Figure 2B:
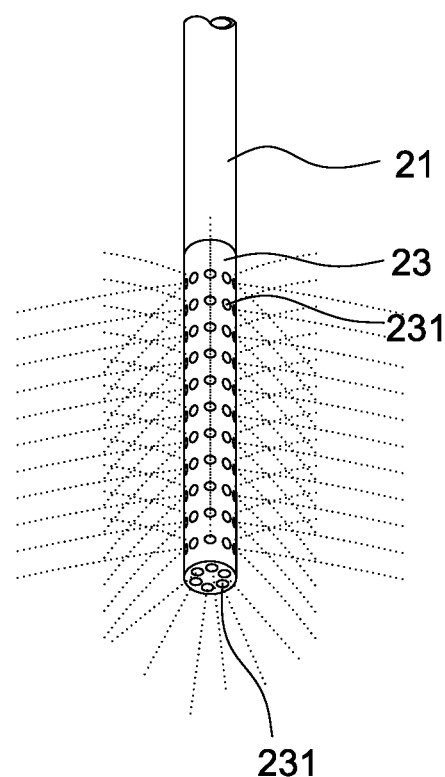
FIG. 2B shows a state of use of the nozzle as disclosed in FIG. 2A.
Figure 3A:
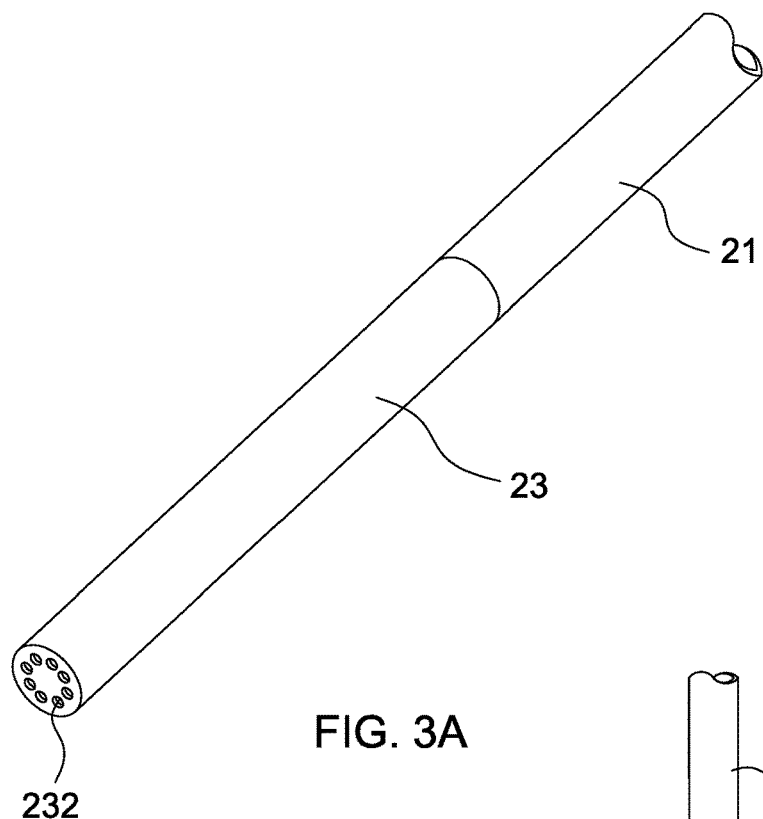
FIG. 3A is an enlarged view of the nozzle in accordance with another embodiment of the present invention.
Figure 3B:
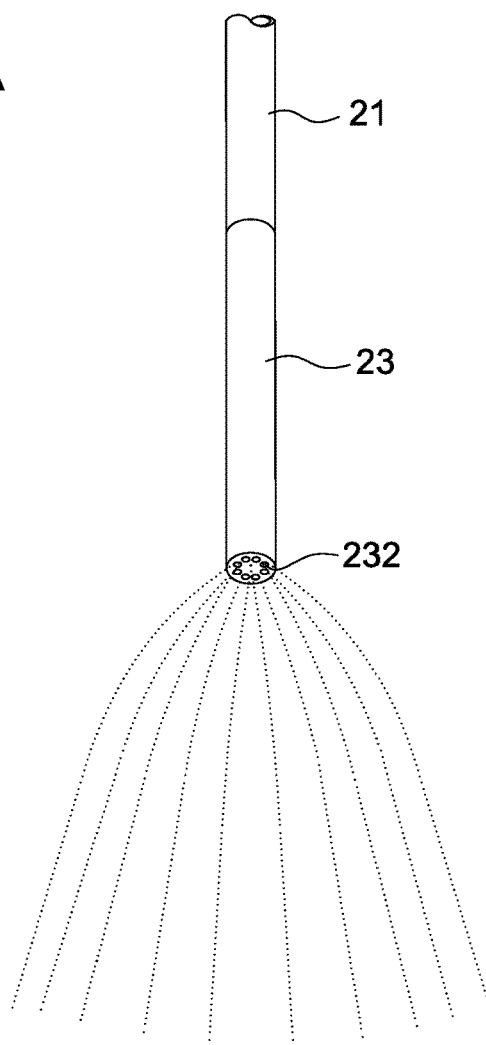
FIG. 3B shows a state of use of the nozzle as disclosed in FIG. 3A.

In some embodiments, the nozzle 23 has different designs which allow the agents to be delivered in different forms such as liquid, gel, emulsion, and viscosity liquid can also be administered in different patterns of application. Referring to FIG. 2A, the nozzle 23 has a plurality of apertures 231 arranged at its end surface and side surface. Such a configuration will enable the agent(s) to be sprayed from both the side surface and the end surface (see FIG. 2B). In this way, the nozzle 23 can spray the agents evenly on a larger area. Furthermore, referring to FIG. 3A, the nozzle 23 only has a plurality of apertures 232 arranged at its end surface. Such a configuration will only enable the agents to be sprayed from the end surface (see FIG. 3B). In this way, the nozzle 23 can spray the agents on a specific area needed to be treated and avoid spraying the agents on areas not needed to be treated. However, in one embodiment, there is a switchable device to switch the apertures; i.e, apertures 231 to apertures 232 or apertures 232 to apertures 231.

In another aspect, the invention provides an antibiotic and/or antimicrobial complex comprising an antibiotic and/or antimicrobial agent cross-linked to or mixed with carriers. The complex provides a specific viscosity conferring high affinity to the gastric mucosal surface. In some embodiments, the complex has a viscosity of, but not limited to, about 3 to 10.000 cp. In some embodiments, the viscosity ranges from about 10 cp to about 800 cp, about 10 cp to about 600 cp, about 10 cp to about 500 cp, about 10 cp to about 400 cp, about 10 cp to about 300 cp, about 10 cp to about 200 cp, about 10 cp to about 100 cp, about 20 cp to about 800 cp, about 20 cp to about 600 cp, about 20 cp to about 500 cp, about 20 cp to about 400 cp, about 30 cp to about 800 cp, about 30 cp to about 600 cp, about 30 cp to about 500 cp, about 30 cp to about 400 cp, about 40 cp to about 1.000 cp, about 40 cp to about 800 cp, about 40 cp to about 600 cp, about 40 cp to about 500 cp, about 40 cp to about 400 cp, about 40 cp to about 300 cp, about 40 cp to about 200 cp, about 40 cp to about 100 cp, about 50 cp to about 1,000 cp, about 50 cp to about 800 cp, about 50 cp to about 600 cp, about 50 cp to about 500 cp, or about 50 cp to about 400 cp.

The examples of such carriers are substances having high affinity to the gastric mucosal surface and selected from the group of various starches (such as potato starch, corn starch, tapioca starch, pea starch), modified starches, sucralfate, carrageenan, locust bean gum, konjac, guar gum, allen gum, arabic gum, alginates, acacia gum, chitosan or polymers (such as polyvinyl alcohol-polyethylene glycol graft copolymer. HPMC, hydroxypropylcellulose, hydroxyethylcellulose, methylcellulose, sodium-carboxymethylcellulose, alkyl cellulose ethers. Carbopol polymers) and a mixture thereof.

According to the invention, the antibiotic and/or antimicrobial agent links to a polymer or mixes with any solution which has high affinity to the gastric mucosal surface to form an antibiotic and/or antimicrobial complex. The complex can prolong the time that the antibiotic and/or antimicrobial agent stays on the gastrointestinal mucosal surface so that the bacteria or microbe in the gastrointestinal tract can be eradicated.

In some embodiments, the antibiotic or antimicrobial agents of the complex include, but are not limited to penicillin, bismuth compound, macrolide, tetracycline, nitroimidazole, quinolone, lincosamide, cephalosporin, rifabutin, furazolidone, or any pharmaceutically acceptable salt thereof and any combinations thereof.

In some embodiments, the penicillins include, but are not limited to, nafcillin, ampicillin, amoxycillin, bacampicillin, hetacillin, penicillin G, penicillin V, pheneticillin, propicillin, methicillin, oxacillin, cloxacillin, dicloxacillin, flucloxacillin, metampicillin, pivampicillin, talampicillin, carbenicillin, carfecillin, carindacillin, sulbenicillin, ticarcillin, azlocillin, mezlocillin, piperacillin, apalcillin, temocillin, mecillinam, pivmecillinam, or any pharmaceutically acceptable salt thereof and any combinations of thereof.

In some embodiments, the bismuth compounds include, but are not limited to, bismuth sugballate, bismuth tannate, bismuth phosphate, bismuth tribromphenate, bismuth subcitrate, bismuth aluminate, bismuth oxide, bismuth salicylate, bismuth subcarbonate, bismuth subnitrate, and mixtures, or any pharmaceutically acceptable salt thereof and any combinations thereof.

In some embodiments, the macrolides include, but are not limited to, miocamycin, rokitamycin, dirithromycin, rosarimycin, erythromycin, spiramycin, oleandomycin, triacetyloleandomycin, clarithromycin, roxithromycin, josamycin, kitsamycin, midecamycin, flurithromycin, azithromycin, or any pharmaceutically acceptable salt thereof and any combinations thereof.

In some embodiments, the tetracyclines include, but are not limited to, methacycline, chlortetracycline, tetracycline hydrochloride, oxytetracycline, doxycycline, demeclocycline, minocycline, or any pharmaceutically acceptable salt thereof and any combinations thereof.

In some embodiments, the nitroimidazoles include, but are not limited to, metronidazole, ornidazole, tinidazole, nimorazole, orthanidazole, or any pharmaceutically acceptable salt thereof and any combinations of thereof.

In some embodiments, the quinolones include, but are not limited to, ciprofloxacin, norfloxacin, enoxacin, fleroxacin, levofloxacin, nadifloxacin, rufloxacin, lomefloxacin, pefloxacin, amifloxacin, sparfloxacin, tosufloxacin, ofloxacin, or any pharmaceutically acceptable salt thereof and any combinations thereof.

In some embodiments, the lincosamides include, but are not limited to, lincomycin, clindamycin, or any pharmaceutically acceptable salt thereof and any combinations of the foregoing.

In some embodiments, the cephalosporins include, but are not limited to, cephalexin, pivcephalexin, cephalothin, cefprozil, cephazolin, cefroxadine, cefadroxiL cefatrizine, cefaclor, cephradine, and the second as well as the third generation cephalosporins such as cephamandole, cefuroxime, cefuroxime axetil, cefonicid, ceforanide, cefotiam, cefotaxime, cefmenoxime, cefodizime, ceftizoxime, cefiximine, cefdinir, cefetamet pivoxil, cefpodoxime proxetil, ceftibuten, ceftazidime, ceftoperazone, cefpiramide, cefsoludin, cefepime, cefpirome, cefiriaxone, and related compounds such as oxycephalosporins including latamoxef and cephamycins such as cefoxitin, cefmetazole, cefotetan, cefbuperazone, cefminox, or any pharmaceutically acceptable salt thereof and any combinations thereof.

In one embodiment, the antibiotic and/or antimicrobial agent is a mixture comprising amoxicillin, clarithromycin and metronidazole. In some embodiments, the amounts of amoxicillin, clarithromycin and metronidazole are about 30% (w/w) to 70% (w/w), about 5% (w/w) to 40% (w/w) and about 10% (w/w) to 50% (w/w), respectively. In one embodiment, the amounts of amoxicillin, clarithromycin and metronidazole are about 45% (w/w) to 55% (w/w), about 10 (w/w) to 20% (w/w) and about 20% (w/w) to 40% (w/w), respectively.

In some embodiments, the antimicrobial agents include, but are not limited to, probiotics, herbal medicines, lilac tea, ingredients of broccoli, or any pharmaceutically acceptable dietary supplement thereof and any combinations of the foregoing thereof.

In another aspect, the invention provides a method for treating a gastrointestinal infection in a subject, comprising the following steps:
(i) providing a system of the invention;
(ii) administering an antibiotic and/or antimicrobial agent or an antibiotic and/or antimicrobial complex to a gastrointestinal tract using the system of the invention.

In one embodiment, before the step (i), the method also comprises a step (i-1) of sublingually administering a proton pump inhibitor to a subject. In another embodiment, before the step (ii), the method further comprises a step (i-2) of administering a mucolytic agent to the gastrointestinal tract of a subject, and/or a step (i-3) of administering an indicator agent targeting an infected site to a subject.

In one embodiment, the step (i-1) involves the administration of a proton pump inhibitor or a patassium competitive acid blocker (P-CAB), such as vonoprazan, to a subject. Such an administration can cause a long-lasting reduction of gastric acid production and thus increase the pH value in the stomach that is unfavorable for *H. pylori* growth. In some embodiments, the proton pump inhibitor includes, but is not limited to, omeprazole, lansoprazole, dexlansoprazole, levolansoprazo, esomeprazole, pantoprazole, and rabeprazole. In a further embodiment, the proton pump inhibitor is lansoprazole. In some embodiments, the patassium competitive acid blocker (P-CAB) includes, but is not limited to, vonoprazan.

In one embodiment, the step (i-2) involves the administration of a mucolytic agent to the gastrointestinal tract of a subject to irrigate and remove gastric mucous so that *H. pylori* can be exposed. A mucolytic agent is an agent able to dissolve thick mucus. In some embodiments, the mucolytic agent includes, but is not limited to, acetylcysteine, ambroxol, carbocisteine, erdosteine, mecysteine, and dornase alfa. In a further embodiment, the mucolytic agent is acetylcysteine. The step (i-2) refers to the administration of a mucolytic agent to the gastrointestinal tract of a subject to remove gastric mucous and expose *H. pylori* on the gastric mucosal surface. In one embodiment, the nozzle of the tube in the endoscope apparatus used in step (i-2) is a shower nozzle. In this regard, acetylcysteine effervescent in water or in alkaline water (pH 9.0) is used to remove gastric mucous.

In one embodiment, the step (i-3) involves the administration of an indicator agent targeting an infected site to a subject. For example, urease is central to the metabolism and virulence of *H. pylori* and necessary for its colonization of the gastric mucosa. Therefore, urease can be used as a target. Urease activity can be determined by a number of ways. As it is known, urease converts urea into ammonium carbonate, which then decomposes into ammonia and carbon dioxide. Consequently, one test for detecting the presence of *H. pylori* includes the steps of contacting a sample of gastric material with a composition containing urea and an indicator, namely a pH indicator that changes color when there is a rise in pH. If urease is present within the gastric material, it breaks down the urea, which results in the formation of ammonia after further decomposition and causes the pH indicator to change color. *H. pylori* urease activity can also be detected by orally administering urea to a subject with subsequent monitoring of the exhaled dioxide and ammonia. U.S. Pat. No. 4,748,113 and U.S. Pat. Applic. No. 20030082664 disclose tests for urease activity, which are incorporated herein by reference.

In some embodiment, the step (i-3) involves the administration of an indicator agent targeting the surface antigen (s) or any structure (s) of *H. pylori*. The anti-*H. pylori* surface antigen includes, but is not limited to, *H. pylori* IgG.

The step (ii) refers to the administration of an antibiotic and/or antimicrobial complex to the stomach of a subject. In one embodiment, the nozzle of the tube in the endoscope apparatus used in step (ii) is a spray nozzle. In this regard, amoxicillin is used to kill bacteria (such as *H. pylori*).

The system, the antibiotic and/or antimicrobial agent and the method of the invention can be used to treat multiple drug resistance bacteria. In one embodiment, the bacteria are *H. pylori*.

The present invention is described in more detail by reference to the following examples, but it should be understood that the invention is not construed as being limited thereto.

EXAMPLES

Clinical Study of the Invention

Ten patients having *H. pylori* infection without prior eradication therapy were enrolled. Before the intraluminal therapy, two tablets of proton pump inhibitor (Takepron) were sublingually administered to the patient. Using the system of the invention, the gastric mucosa was irrigated with acetylcysteine (12 mg/ml) solution to remove the acid and mucous on the gastric mucosa. The pH levels before and after irrigation were measured. The acidity of the gastric juice could be well controlled at around pH 5.0 after irrigation. The total dosage of acetylcysteine was less than 140 mg/kg. Then amoxicillin, metronidazole, clarithromycin, sucrate gel and distilled water were mixed to form a complex. The complex had a viscosity of about 50 to 5,000 cp, conferring high affinity to the gastric mucosal surface. The viscosities of the complexes were shown below.

TABLE A

Speed: 50 RPM; Spindle: S31

| sucrate gel (%) | Viscosity (cp) |
| --- | --- |
| 57.4 | 345 |
| 57.7 | 346.8 |
| 59 | 354 |
| 58.03333 | 348.6 |

TABLE B

Speed: 100 RPM; Spindle: S31

| sucrate gel (%) | Viscosity (cp) |
| --- | --- |
| 57.3 | 172.2 |
| 58 | 174 |
| 56.9 | 170.7 |
| 57.4 | 172.3 |

TABLE C

Speed: 50 RPM; Spindle: S18

| sucrate gel (%) | Viscosity (cp) |
| --- | --- |
| 86.1 | 51.66 |
| 85.9 | 51.54 |
| 86.1 | 51.66 |
| 86.03333 | 51.62 |

The complex was dispensed to the surface of the gastric mucosa and the duodenal mucosa of the duodenal bulb as evenly as possible using the system of the invention. The treatment could be completed within 15 minutes. After the above intraluminal therapy, the *H. pylori* infection of 9 patients (90%) was eradicated, as confirmed by the urea breath tests performed six weeks later after the treatment.

| Patient No. | Irrigation time (minute:second) | Complex administration time (minute:second) | Total treatment time (minute:second) |
|---|---|---|---|
| 1 | 00:06:44 | 00:04:13 | 00:10:57 |
| 2 | 00:07:07 | 00:04:39 | 00:11:46 |
| 3 | 00:05:17 | 00:04:32 | 00:09:49 |
| 4 | 00:05:45 | 00:04:33 | 00:10:18 |
| 5 | 00:06:46 | 00:05:46 | 00:12:32 |
| 6 | 00:07:40 | 00:05:20 | 00:13:00 |
| 7 | 00:05:23 | 00:05:58 | 00:11:21 |
| 8 | 00:06:25 | 00:04:45 | 00:11:10 |
| 9 | 00:03:08 | 00:04:58 | 00:08:06 |
| 10 | 00:05:45 | 00:04:52 | 00:10:37 |

Around 3-6 months after the treatment, the stool *H. pylori* antigen examinations also showed negative in all the eradicated patients, which indicated that *H. pylori* infections did not recur and *H. pylori* did not reside in the patients' intestines.

| Patient No. | Stool HPAg after 3-6 months (+, −) |
|---|---|
| 1 | negative |
| 3 | negative |
| 4 | negative |
| 5 | negative |
| 6 | negative |
| 7 | negative |
| 8 | negative |
| 9 | negative |
| 10 | negative |

The study confirms that the present invention is currently the only effective and safe therapy system that could immediately eradicate *H. pylori* infection with a single dose regimen.

What is claimed is:

1. A method for treating a gastrointestinal infection in a subject, comprising the following steps:
   (i) providing a system for dispensing one or more agents to a subject's gastrointestinal tract;
   wherein the system comprises:
   an endoscope apparatus comprising:
      a light guide device;
      an operation section connected to the light guide device;
      an insertion tube connected to the operation section;
      a bending section connected to the insertion tube; and
      a working channel formed within the operation section, the insertion tube and the bending section;
   wherein said working channel has an opening formed at the operation section and another opening formed at an end of the bending section; and
   an agent dispenser, comprising:
      a pump for pumping an agent;
      a catheter, wherein one end of the catheter connects to the pump so that the catheter could be used for delivering the agent pumped from the pump; and
      a nozzle connected to the other end of the catheter;
      wherein said catheter extends into the working channel via the opening formed at the operation section and passes through the working channel, then extends outward from the working channel via the opening formed at the end of the bending section;
   (ii) administering first antibiotic and/or antimicrobial agent or an antibiotic and/or antimicrobial complex to a gastrointestinal tract using the medical devices, including the endoscope apparatus of the system;
   wherein the antibiotic and/or antimicrobial complex comprises a second antibiotic or antimicrobial agent linked to a polymer or mixed with any solution which has high affinity to the gastric mucosal surface; and
   wherein the antibiotic or antimicrobial complex has a viscosity of 3 to 10,000 cp.

2. The method of claim 1, wherein before the step (i), the method can also comprise a step of (sublingually) administering a proton pump inhibitor or a potassium competitive acid blocker (P-CAB) to a subject.

3. The method of claim 1, wherein before the step (ii), the method can further comprise a step of administrating a mucolytic agent to the gastrointestinal tract of a subject.

4. The method of claim 3, wherein said mucolytic agent is acetylcysteine, ambroxol, carbocisteine, erdosteine, mecysteine, or dornase alfa.

5. The method of claim 1, wherein before the step (ii), the method can further comprise a step of administering an indicator agent targeting an infected site to a subject.

6. The method of claim 5, wherein said indicator agent is urea or ammonia or carbon dioxide or a pH indicator, or any bacterial surface and/or structural binding agent(s) for H. pylori.

7. The method of claim 1, wherein said second antibiotic or antimicrobial agent of the complex is penicillin, bismuth compound, macrolide, tetracycline, nitroimidazole, quinolone, lincosamide, cephalosporin, rifabutin, furazolidone, or any pharmaceutically acceptable salt thereof and any combinations thereof.

8. The method of claim 7, wherein said penicillin is nafcillin, ampicillin, amoxycillin, bacampicillin, hetacillin, penicillin G, penicillin V, pheneticillin, propicillin, methicillin, oxacillin, cloxacillin, dicloxacillin, flucloxacillin, metampicillin, pivampicillin, talampicillin, carbenicillin, carfecillin, carindacillin, sulbenicillin, ticarcillin, azlocillin, mezlocillin, piperacillin, apalcillin, temocillin, mecillinam, pivmecillinam, or any pharmaceutically acceptable salt thereof and any combinations of thereof.

9. The method of claim 7, wherein said bismuth compound is bismuth sugballate, bismuth tannate, bismuth phosphate, bismuth tribromphenate, bismuth subcitrate, bismuth aluminate, bismuth oxide, bismuth salicylate, bismuth subcarbonate, bismuth subnitrate, mixtures, or any pharmaceutically acceptable salt thereof and any combinations thereof.

10. The method of claim 7, wherein said macrolide is miocamycin, rokitamycin, dirithromycin, rosarimycin, erythromycin, spiramycin, oleandomycin, triacetyloleandomycin, clarithromycin, roxithromycin, josamycin, kitsamycin, midecamycin, flurithromycin, azithromycin, or any pharmaceutically acceptable salt thereof and any combinations thereof.

11. The method of claim 7, wherein said tetracycline is methacycline, chlortetracycline, tetracycline hydrochloride, oxytetracycline, doxycycline, demeclocycline, minocycline, or any pharmaceutically acceptable salt thereof and any combinations thereof.

12. The method of claim 7, wherein said nitroimidazole is metronidazole, ornidazole, tinidazole, nimorazole, orthanidazole, or any pharmaceutically acceptable salt thereof and any combinations of thereof.

13. The method of claim 7, wherein said quinolone is ciprofloxacin, norfloxacin, enoxacin, fleroxacin, levofloxacin, nadifloxacin, rufloxacin, lomefloxacin, pefloxacin, amifloxacin, sparfloxacin, tosufloxacin, ofloxacin, or any pharmaceutically acceptable salt thereof and any combinations thereof.

14. The method of claim 7, wherein said lincosamide is lincomycin, clindamycin, or any pharmaceutically acceptable salt thereof and any combination thereof.

15. The method of claim 7, wherein said cephalosporin is cephalexin, pivcephalexin, cephalothin, cefprozil, cephazolin, cefroxadine, cefadroxil, cefatrizine, cefaclor, cephradine, and the second as well as the third generation cephalosporins such as cephamandole, cefuroxime, cefuroxime axetil, cefonicid, ceforanide, cefotiam, cefotaxime, cefmenoxime, cefodizime, ceftizoxime, cefiximine, cefdinir, cefetamet pivoxil, cefpodoxime proxetil, ceftibuten, ceftazidime, ceftoperazone, cefpiramide, cefsoludin, cefepime, cefpirome, cefiriaxone, and related compounds such as oxycephalosporins including latamoxef, and cephamycins such as cefoxitin, cefmetazole, cefotetan, cefbuperazone, cefminox, or any pharmaceutically acceptable salt thereof and any combinations thereof.

16. The method of claim 7, wherein the antibiotic and/or antimicrobial complex is a mixture comprising amoxicillin, clarithromycin and metronidazole.

17. The method of claim 1, wherein said pump can provide a desired pressure that is adjustable depending on a need in treatment and/or a patient's condition.

18. The method of claim 1, wherein said pump provides a pressure ranging from 0.13 MPa to 70 MPa.

* * * * *